United States Patent [19]

Braun, III

[11] Patent Number: 6,087,162
[45] Date of Patent: Jul. 11, 2000

[54] TRANSGENIC PLANTS RESISTANT TO GEMINIVIRUS INFECTION

[75] Inventor: Carl Joseph Braun, III, Woodland, Calif.

[73] Assignee: Seminis Vegetable Seeds, Inc., Saticoy, Calif.

[21] Appl. No.: 08/643,779

[22] Filed: May 6, 1996

[51] Int. Cl.$^7$ .............................. C12N 15/00; C12N 5/14; A01H 4/00; C07K 14/005

[52] U.S. Cl. .................... 435/320.1; 435/69.1; 435/70.1; 435/71.2; 435/235.1; 435/410; 435/418; 435/419; 536/23.1; 536/23.72; 536/24.1; 530/350; 800/278; 800/279; 800/280; 800/288; 800/294; 800/301

[58] Field of Search ................................ 435/419, 235.1, 435/320.1, 69.1, 70.1, 71.2, 410, 418; 536/23.1, 23.72, 24.1; 800/205, 278, 279, 280, 288, 294, 301; 530/350

[56] References Cited

FOREIGN PATENT DOCUMENTS

WO 96/08573  3/1996  WIPO .

OTHER PUBLICATIONS

Fields Virology, 3rd Ed., vol. 1, Chap 17, pp. 507–508, 1996.

Aono et al. Plant Cell Physiol. vol. 32(5), pp. 691–697, 1991.

Sondra G. Lazarowitz, "Geminiviruses: Genome Structure and Gene Function," *Critical Reviews in Plant Sciences*, 11(4): 327–349 (1992).

R. Van Blokland, N. Van der Geest, J.N.M. Mol and J.M. Kooter, "Transgene–mediated Suppression of Chalcone Synthase Expression in Petunia Hybrida Results from an Increase in Rna Turnover," *The Plant Journal*, 6(6):861–877 (1994).

F. De Kouchkovsky, I. Jupin, L. Wartig, M. Bendahmane, A. Kheyr–Pour, F. Jouanneau, G.P. Accotto, V. Matzeit and B. Gronenborn, "Molecular Biology of Tomato Yellow Leaf Curl Virus (TYLCV) and Potential Ways to Control the Disease," *Molecular Biology of the Tomato: Fundamental Advances and Crop Improvement*, Editor John Yoder, Techromic Publishers, (1993) pp. 227–237.

Kunkel et al., "Rapid and Efficient Site–Specific Mutagenesis without Phenotypic Selection", *Recombinant DNA Methodology*, 1989, pp. 587–601.

Gilbertson et al., "Differentiation of Bean–Infecting Geminiviruses by Nucleic Acid Hybridization Probes and Aspects of Bean Golden Mosaic in Brazil", *Plant Disease*, vol. 75, No. 4, 1991, pp. 336–342.

Gilbertson et al., "Pseudorecombination between infectious cloned DNA components of tomato mottle and bean dwarf mosaic geminiviruses", *Journal of General Virology*, vol. 74, 1993, pp. 23–31.

Navot et al., "Tomato Yellow Leaf Curl Virus: A Whitefly–Transmitted Geminivirus with a Single Genomic Component", *Virology*, vol. 185, 1991, pp. 151–161.

Faria et al., "Beam Golden Mosaic Geminivirus Type II Isolates from the Dominican Republic and Guatemala: Nucleotide Sequences, Infectious Pseudorecombinants, and Phylogenetic Relationships", *The American Phytopathological Society*, vol. 84, No. 3, 1994, pp. 321–329.

Torres–Pacheco et al., "Complete nucleotide sequence of pepper huasteco virus: analysis and comparison with bipartite geminivirus", *Journal of General Virology*, vol. 74, 1993, pp. 2225–2231.

Kunik et al., "Transgenic Tomato Plants Expressing the Tomato Yellow Leaf Curl Virus Capsid Protein are Resistant to the Virus", *Bio/Technology*, vol. 12, May 1994, pp. 500–504.

Hanson et al., "Mutational Analysis of a Putative NTP–Binding Domain in the Replication–Associated Protein (AC1) of Bean Golden Mosaic Geminivirus", *Virology*, vol. 211, 1995, pp. 1–9.

Noris et al., "Resistance to Tomato Yellow Leaf Curl Geminivirus in *Nicotiana benthamiana* Plants Transformed with a Truncated Viral C1 Gene", *Virology*, vol. 224, 1996, pp. 130–138.

Bendahmane et al., "Engineering resistance against tomato yellow leaf curl virus (TYLCV) using antisense RNA", *Plant Molecular Biology*, vol. 33, 1997, pp. 351–357.

*Primary Examiner*—Phuong T. Bui
*Attorney, Agent, or Firm*—Rockey, Milnamow & Katz, Ltd.

[57] ABSTRACT

A method for producing genetically transgenic plants exhibiting resistance to a geminivirus such as tomato yellow leaf curl virus. In another aspect, the invention embraces chimeric plant genes, cassettes containing the chimeric plant genes, heterologous DNA segments containing the cassettes, and genetically transgenic cells and differentiated plants which exhibit resistance to geminiviruses. In yet another aspect, the invention embraces bacterial cells and plant transformation vectors comprising a heterologous DNA segment encoding for resistance to geminiviruses.

1 Claim, No Drawings

TRANSGENIC PLANTS RESISTANT TO GEMINIVIRUS INFECTION

BACKGROUND OF THE INVENTION

Geminiviruses present the most serious disease problem in many vegetable crops in tropical and subtropical regions. Brown et al. (1992) *Plant Disease*, 76:220–225. Major epidemics of geminivirus infections of beans and tomatoes have recently occurred in Florida, the Caribbean Basin, Mexico, Central America, Southern Europe, the Jordan Valley and Turkey. Unfortunately, traditional breeding methods have failed to produce cultivars with significant levels of resistance to geminiviruses.

Geminiviruses are characterized by a covalently closed circular single-stranded DNA genome (css-DNA) that infect both monocotyledonous and dicotyledonous plants. These viruses occur as twinned ("geminate") icosahedral particles. Geminiviruses are traditionally classified into two major subgroups, based on their insect vector, host range, and genome organization. Padidam et al. (1995) *J Gen. Virol.* 76:249–263. The first subgroup includes leaf-hopper transmitted viruses that infect mainly monocotyledonous plants and possess a single monopartite genome. The second subgroup includes viruses that are transmitted by a whitefly (*Bemisia tabaci*), infect dicotyledonous plants and possess a bipartite genome. A third subgroup has also been discovered and includes geminiviruses that have properties intermediate between the previously described two subgroups.

For example, the tomato yellow leaf curl virus (TYLCV) is one of the most devastating virus diseases of cultivated tomato (*Lycopersicon esculentum*). Tomato yellow leaf curl virus is a subgroup III whitefly transmitted geminivirus that contains a single monopartite genome. Navot, N. et al., (1991) *Virology*, 151–161. However, the cloning of a TYLCV-like whitefly-transmitted geminivirus with a bipartite genome from Thailand has also been reported. See Rochester, D. E., et al., (1990) *Virology*, 520–526.

The TYLCV genome contains 6 open reading frames. Open reading frames, V1 and V2, are located on the virion (plus) strand. The four remaining open reading frames, C 1, C2, C3 and C4, are located on the complementary (minus) strand. The C2 open reading frame partially overlaps with the C1 and C3 open reading frames; C4 is completely covered by the overlapping C1 gene. The C1 open reading frame is sometimes referred to as AC1.

Complete or partial sequence data are available for several TYLCV isolates. For example, the genome of an Israeli isolate of TYLCV has been cloned and sequenced. Navot, N. et al., (1991) *Virology*, 151–161. Sequence data are also available for TYLCV isolates from Sardinia. Kheyr-Pour, A., et al., (1991) *Nucl. Acids Res.*, 19:6763–6769. The Australian isolate of TYLCV was disclosed in Dry et al. (1993) *J Gen. Virol.* 74:147–151. The sequence of the Thailand isolate was published by Rochester (1994) *J. Gen. Virol.* 75:477–485. An additional Thailand isolate was disclosed by S. Attathom to Padidam et al. (1995) *J. Gen. Virol.* 76:249–263. Egyptian and Sicilian isolates were similarly disclosed to Padidam et al. (1995) *J. Gen. Virol.* 76:249–263 by N. Abdallah and G. Accotto, respectively.

The object of the present invention is to produce transgenic plants that are resistant to geminivirus infection, such as, but not limited to, infection by the tomato yellow leaf curl virus. An additional object of the present invention is to provide methods for creating transgenic plants resistant to geminivirus infection.

SUMMARY OF THE INVENTION

The present invention involves transgenic plants which are resistant to geminivirus infection, such as, but not limited to, infection by tomato yellow leaf curl virus (TYLCV). These transgenic plants contain in their chromosomal DNA, geminivirus DNA. The geminivirus DNA encodes at least one of the six open reading frames. For example, plants resistant to infection by TYLCV would contain TYLCV DNA in their chromosomal DNA. The TYLCV DNA, may be any portion of the viral genome, such as, but not limited to, the C1 and C4 open reading frames and portions of the C2 and C3 open reading frames. The present invention also includes methods for making plants resistant to a geminivirus infection.

The present invention involves a chimeric plant gene that contains two or three elements in sequence. The first element, is a promoter DNA segment, which is optional, but, if present, functions in plant cells. The second element is a DNA sequence encoding at least open reading frame of a geminivirus. The third element of the chimeric gene is a 3' non-translated termination segment. The promoter DNA segment, if present, and the 3' non-translated termination segment are operatively linked to the DNA sequence.

The promoter DNA segment, if present, may be a constitutive promoter such as the cauliflower mosaic virus 35S promoter, the octopine synthase promoter, the nopaline synthase promoter and the mannopine synthase promoter with octopine synthase activators. Other promoters which function in plant cells can be used as well.

The DNA sequence encodes at least one open reading frame of a geminivirus. If the geminivirus is TYLCV, it is desired that the DNA sequence encode the C1 and C4 open reading frame and portions of the C2 and C3 open reading frames.

The 3' non-translated termination segment may be the 3' non-translated termination segment of the nopaline synthase gene (NOS-T). However, those skilled in the art will recognize that other terminators can be used.

The present invention also involves a cassette containing the chimeric plant gene described above as well as a heterologous DNA segment containing said cassette. Plants transformed with said heterologous DNA segment are also contemplated.

Additionally, the present invention involves a method of producing plants resistant to infection by a geminivirus, such as, but not limited to infection by tomato yellow leaf curl virus. The method involves first constructing a heterologous DNA segment comprising at least one cassette. The one cassette that must be present is referred to as an "effect" cassette. The effect cassette confers geminivirus resistance to a plant and contains a chimeric gene capable of expression in a plant cell. The chimeric gene contains two or three elements. The first element is a promoter DNA segment, which is optional, but, if present, functions in plant cells. The second element is a DNA sequence that encodes at least one of the six reading frames of geminivirus. For example, if the geminivirus is TYLCV, it is desired that the DNA sequence encode the C1 and C4 open reading frames and portions of the C2 and C3 open reading frames. The third element is a 3' non-translated termination segment. The promoter DNA segment, if present, and the 3' non-translated termination segment are operatively linked to the geminivirus DNA sequence.

The promoter DNA segment, if present, may be a constitutive promoter such as the cauliflower mosaic virus 35S promoter, the octopine synthase promoter, the nopaline synthase promoter and the mannopine synthase promoter with octopine synthase activators. Other promoters which function in plant cells can be used as well.

The 3' non-translated termination segment may be the 3' non-translated termination segment of the nopaline synthase gene (NOS-T). However, those skilled in the art will recognize that other terminators can be used.

Additionally, the heterologous DNA segment may contain additional cassettes. For example, the heterologous DNA segment may contain two cassettes. As discussed earlier, the first cassette is the "effect" cassette that contains a chimeric gene.

The second cassette may be a "selectable marker" cassette that contains a chimeric gene capable of expression in a plant cell. The chimeric gene contains three elements. The first element is a second promoter DNA segment that functions in plant cells. The second element is a DNA sequence that encodes for the expression of a protein which allows for selection of plant cells containing said cassette. The protein may encode antibiotic or herbicide resistance. For example, the protein may encode the enzyme neomycin phosphotransferase II. The third element is a second 3' non-translated termination segment.

The promoter of the effect cassette, if present, and the promoter of the selectable marker cassette may be the same or different. In addition, these promoters may be constitutive promoters such as the cauliflower mosaic virus 35S promoter, the octopine synthase promoter, the nopaline synthase promoter and the mannopine synthase promoter with octopine synthase activators. Other promoters which function in plant cells can be used as well.

The 3' non-translated termination segment of the effect and selectable marker cassettes may be the same or different. The 3' non-translated termination segment may be the 3' non-translated termination segment of the nopaline synthase gene (NOS-T). However, those skilled in the art will recognize that other terminators can be used.

The effect cassette as well as any other cassettes, such as a selectable marker cassette, are linked together in the heterolgous DNA segment. Plant cells are then transformed with this heterologous DNA segment. Transgenic plant cells containing this heterologous DNA segment are selected from non-transgenic plant cells that do not contains this heterologous DNA segment and then regenerated into transgenic plants which are resistant to geminivirus infection.

The present invention also involves plants produced by the above described methods and seed produced by these plants.

Finally, the present invention involves a plasmid vector containing the entire C 1 and C4 open reading frame and portions of the C2 and C3 open reading frame of TYLCV comprising a plasmid designated pETO 129 having American Type Culture Collection Accession Number 97526.

DETAILED DESCRIPTION OF THE INVENTION

The present invention involves transgenic plants that are resistant to geminivirus infection. More specifically, the invention provides transgenic plants that are resistant to infection by tomato yellow leaf curl virus (TYLCV). These transgenic plants contain chromosomal DNA, geminivirus DNA encoding at least one of the six open reading frames. For example, plants resistant to infection by TYLCV would contain TYLCV DNA integrated into the plant chromosomal DNA. The TYLCV DNA may be any portion of the viral genome, such as, but not limited to, the C1 and C4 open reading frames and portions of the C2 and C3 open reading frames. The invention also includes methods for making plants resistant to infection by a geminivirus, especially infection by TYLCV.

In order to obtain plants that are resistant to TYLCV, plant cells are transformed with a heterologous, recombinant DNA segment which contains at least one cassette. As used herein, "plant cells" encompasses any material from a plant that has a nucleus and cytoplasm surrounded by a membrane. It includes plants grown in a culture medium as cell suspensions, microspores, protoplasts or explants. Also as used herein, "heterologous" refers to a cassette that is not present in a non-transgenic cell. As also used herein, a "cassette" refers DNA segments that are operatively linked. Many different types of cassettes are well known and used by those of ordinary skill in the art. As used herein, an "effect" cassette refers to a DNA segment that contains a chimeric gene having two or three elements. The first element is a promoter, which is optional. The second element is a DNA sequence that encodes a geminivirus gene or genes. The third element is a 3' non-translated region. The purpose of the "effect" cassette as used herein is to confer resistance to geminiviruses. Also as used herein, a "selectable marker" cassette refers to a DNA segment that contains a chimeric gene having three elements. The first element is a promoter. The second element is a DNA sequence that encodes for the expression of protein which allows for selection of cells containing said cassette from cells that do not contain said cassette. The third element is a 3' non-translated region. Finally, as also used herein, "transgenic plant" refers to a plant that contains chromosomally integrated foreign or heterologous DNA. The transgenic plant cells of this invention contain a heterologous, recombinant DNA segment which contains at least one cassette.

In order to produce plants that are resistant to geminivirus infection, plant cells must be transformed with a heterologous DNA segment that contains at least one cassette. The one cassette that must be present is an effect cassette which contains a chimeric gene having two or three elements. The first element that the chimeric gene contains is a first promoter DNA segment, which is optional, but, if present, functions in plant cells. The second element is a DNA sequence that encodes at least one of the six open reading frames of a geminivirus. For example, if resistance to infection from TYLCV is to be conferred, it is preferred that the DNA sequence encode the entire C 1 and C4 open reading frame and portions of the C2 and C3 open reading frame of TYLCV. The third element that the chimeric gene contains is a first 3' non-translated termination segment. The promoter DNA segment, if present, and the 3' non-translated termination segment are operatively linked to the DNA sequence.

If present, any promoter DNA segment can be used in the effect cassette provided that it functions in plant cells. Suitable promoters include those which are derived from a gene which is naturally expressed in plants and synthetic promoter sequences which may include redundant or heterologous enhancer sequences. For example as discussed earlier, constitutive promoters such as the Cauliflower Mosaic Virus 35S promoter, the octopine synthase promoter the nopaline synthase promoter and the mannopine synthase promoter with octopine synthase activators can be used as well.

Nucleotide sequences encoding one or more open reading frames from any geminivirus can be used in this invention. For example, the nucleotide sequences of TYLCV can be used in this invention. Nucleotide sequences of several TYLCV isolates have been cloned and sequenced. Many of these sequences have either been published, disclosed and/or deposited in Genbank as indicated below.

| TYLCV isolate | Publication | Genbank Accession |
| --- | --- | --- |
| Austrailian isolate | Dry et al. (1993) J. Gen. Virol. 74:147–151 | S53251 |
| Indian isolate 1 | — | U15015 U15017 |
| Indian isolate 2 | | U15016 |
| Israeli isolate | Navot et al. (1991) Virology 185:151–161 | X15656 |
| Sardinia isolate | Kheyr-Pour et al. Nucl. Acids Res. 19:6763–6769 | X61153 |
| Thailand isolate 1 | Rochester (1994) J. Gen. Virol. 75: 477–485 | M59838 M59839 |

In addition to the sequences deposited in Genbank, other isolates have been sequenced and disclosed. For instance, a second isolate from Thailand, Thailand isolate 2, has been sequenced and was disclosed to Padidam et al. (1995) *J. Gen. Virol.* 76:249–263 by S. Attahthom. Likewise, the sequence of an Egyptian isolate was also disclosed to Padidam et al. (1995) *J. Gen. Virol* 76:249–263 by N. Abdallah.

The comparison of geminivirus sequences shown in Padidam et al. (1995) *J. Gen. Virol.*, 76:249–263 describes the relative similarities between various TYLC geminiviruses. For example, Padidam et al. (1995) *J Gen. Virol*, 76:249–263 state on page 254 that a high degree of identity (91–99%) was observed between the following pairs of tomato yellow leaf curl viruses: Indian isolate 1 and Indian isolate 2, the Egyptian isolate and the Israeli isolate, the Sicilian isolate and the Sardinian isolate and the Thailand isolate 1 and Thailand isolate 2. These comparisons are useful in designing strategies to clone TYLCV genes for use in this invention.

From these published and/or Genbank sequences, synthetic nucleotide sequences for each of these TYLCV isolates can be prepared and used to create a DNA segment that encodes for at least one of the six open reading frames of TYLCV. The creation of synthetic sequences using a DNA Synthesizer are well known in the art. Additionally, plasmids containing these sequences can also be used in this invention to create the DNA sequence. Furthermore, an uncharacterized TYLCV isolate can also be used to create the DNA sequence of this invention. In this instance, TYLCV DNA is isolated from infected tissue and purified using techniques well known to those skilled in the art. If the virus is isolated in a region close to where a viral isolate has been sequenced, one can use the published sequence to design primers to clone the desired open reading in the characterized TYLCV isolate by PCR.

The nucleotide sequence from any geminivirus isolate can be used to create a DNA sequence that encodes for at least one of the six open reading frames from that geminivirus. One or more of the open reading frames may be encoded by the DNA sequence. For example, to confer resistance to TYLCV infection, the DNA sequence that encodes the entire C1 and C4 open reading frames and portions of the C2 and C3 open reading frames may be used. When the C1 open reading frame of TYLCV was cloned, portions of the C2 and C3 open reading frame were obtained. These portions of the C2 and C3 open reading frame may be altered to remove their coding capacity or kept. If they are kept, the DNA segment will contain or encode the C1 and C4 open reading frames as well as portions of the C2 and C3 open reading frames of TYLCV.

The effect cassette also contains a first 3' non-translated termination segment that is operatively linked to the 3' end of the coding region of the DNA sequence. The termination segment should have a polyadenylation signal which functions to cause the addition of polyadenylate nucleotides to the 3' end of the mRNA. Several termination segments useful in plants are well known and can be used herein. One example is the 3' non-translated region of the nopaline synthase gene (NOS-T), (Fraley et al., (1983) *PNAS* 80:4803–4807). Another terminator is the 3' non-translated region of the pea rbcS-E9 gene, which can also be used (Coruzzi et al., (1984) *EMBO J.* 1671–1679).

In addition to the effect cassette, the heterologous DNA segment may also contain additional cassettes, such as, but not limited to, a selectable marker cassette. A selectable marker cassette allows for the selection of transgenic plant cells containing said selectable marker cassette from non-transgenic plant cells that do not contain the cassette. The use of selectable markers is well known to those of ordinary skill in the art for use in selecting transgenic plant cells from non-transgenic plant cells.

The selectable marker cassette contains a chimeric gene that is composed of three elements. The first element is a promoter DNA segment which functions in plant cells. The second element is a DNA sequence that encodes for the expression of a protein which allows for selection of transgenic plant cells containing said cassette from non-transgenic plant cells that do not contain said cassette. For example, the DNA sequence may encode a protein giving antibiotic or herbicide resistance. Additionally, the DNA sequence may encode for an enzyme which allows for the carbohydrate based selection of transgenic plants as described in WO 93/05163 and WO 94/20627, hereby incorporated by reference. The third element is a 3' non-translated termination region.

The selectable marker cassette contains a promoter DNA segment that is operatively linked to the DNA segment. Any promoter segment can be used in this cassette provided that it functions in plant cells and controls the expression of the DNA sequence. Suitable promoters may include both those which are derived from a gene that is naturally expressed in plants and synthetic promoter sequences which may include redundant or heterologous enhancer sequences. For example, a constitutive promoter can be used such as the Cauliflower Mosaic Virus (CaMV) 35S promoter, the octopine synthase promoter (P-OCS), the nopaline synthase promoter (P-NOS), the small subunit of ribulose bisphosphate carboxylase oxygenase (ssRUBISCO) and the mannopine synthase promoter with octopine synthase activators can also be used. The promoter selected should be capable of causing sufficient expression to result in the production of an effective amount of protein necessary to allow for selection of transgenic plant cells containing said selectable marker casssette from non-transgenic plant cells which do not contain said selectable marker cassette. The promoter in the selectable marker cassette may be the same or different than the promoter used in the effect cassette.

The DNA sequence that can be used is any DNA sequence that encodes for a protein which allows for the selection of transgenic plant cells containing said selectable marker cassette from non-transgenic plant cells that do not contain this selectable marker cassette. For example, the DNA sequence may encode for a protein giving resistance or tolerance to an antibiotic or herbicide. For example, the DNA sequence may encode for the enzyme neomycin phosphotransferase type II, which when expressed in most plant cells in sufficient quantities, confers resistance of those plant cells to the antibiotic kanamycin; the DNA sequence may also encode for acetyl lactate synthase, which when expressed in most plant cells in sufficient quantities, confers resistance of those plant cells to the herbicide chlorsulfuron. The nucleotide sequence encoding neomycin phosphotransferase type II gene is well known in the art. Additionally, other DNA sequences that are known to encode for antibiotic resistance can also be used.

The selectable marker cassette also contains a 3' non-translated termination segment that is operatively linked to the 3' end of the coding region of the DNA segment. Like the 3' non-translated DNA segment used in the effect cassette, the termination segment used in the selectable marker cassette should have a polyadenylation signal which functions to cause the addition of polyadenylate nucleotides to the 3' end of the mRNA. Any termination segment useful in plants can be used, such as the 3' non-translated termination region of the nopaline synthase gene or the 3' non-translated region of the pea rbcS-E9. Additionally, the 3' non-translated termination segment used in the selectable marker cassette may be the same or different than the 3' non-translated termination segment used in the effect cassette.

The effect cassette as well as any other cassettes, such as a selectable marker cassette, are linked together in the heterologous DNA segment so that the cassettes constitute very tightly linked loci that are transformed into the plant's chromosomal DNA. Thus, transformation of plants cells with one of the cassettes is very strongly correlated with transformation with the other cassette.

The recombinant heterologous DNA segment is then inserted into a vector for use in this invention. The most efficient vectors for use in this invention are binary vectors. The salient feature of the binary plasmid is that after infection by an *Agrobacterium tumefaciens* harboring the plasmid, a part of the plasmid DNA is integrated into the plant chromosomal DNA. The segments that direct this insertion are referred to as the T-DNA right and left borders. The right and left T-DNA borders can be as small as 25 base pairs in length. The use of Agrobacterium-mediated gene transfer to introduce DNA into plant cells is well known in the art (Fraley et al., (1985) *Bio/Technology*, 3:629; and Rogers et al., (1987) *Meth. Enzymol.*, 153:253–277).

Recent technological advances in vectors for Agrobacterium-mediated gene transfer have improved the arrangement of genes and restriction sites in vectors to facilitate construction of vectors capable of expressing various genes. The vectors described by Hajdukiewicz et al., (1994) *Plant Mol. Biol.* 25:989–994, which have convenient multi-linker regions can be used in this invention.

One skilled in the art would also recognize that other vectors could be used. The recombinant heterologous DNA segment can be introduced into monocotyledonous or dicotyledonous plant cells or tissues using other techniques such as electroporation, microprojectile bombardment, and microinjection.

Once a suitable vector has been constructed, and transformed into an appropriate Agrobacterium strain, plant cells or tissues can be transformed with recombinant heterologous DNA segment containing cassettes of interest. This involves culturing plant cells or tissues from the target plant. For example, if tomato plants are to be transformed, seeds from the tomatoes targeted for transformation are collected, sterilized, rinsed in distilled water and then germinated on an agar surface for approximately 72 hours in the dark at approximately 25° C. The seeds are then moved to a lighted area under approximately 80 micromol·m$^{-2}$·s$^{-1}$ PPFD at 24–26° C. Plant tissue that is to be used for transformation is prepared by removing it from the seedlings and cutting into parts suitable for transformation with a vector described above.

If the vectors are binary vectors containing both an effect cassette and a selectable marker cassette in the appropriate strain of *Agrobacterium tumefaciens*, the excised plant parts, which are called explants, are co-cultivated with the bacteria. After the explants are co-cultivated with the *Agrobacterium tumefaciens* harboring the binary plasmid, they are transferred to a regeneration medium that is supplemented with an appropriate antibiotic, such as carbenicillin, to eliminate the bacteria. After a period of approximately two to four weeks, explants are moved to a fresh medium. Transgenic plant cells are then selected from the non-transgenic plant cells and regenerated into transgenic plants.

Transgenic plants (T0) recovered from tissue culture are selfed and the seed (T1) collected. To test for resistance to TYLCV, T1 seedlings are grown to approximately the two to three leaf stage and then inoculated. Many forms of inoculation can be used. The use of Agro-inoculation, for example, is well known to those of ordinary skill in the art. Agro-inoculation involves injecting the young plants with a solution containing a disarmed Agrobacterium to deliver the viral DNA. The injected Agrobacterium contains a full, or at least partial tandem repeat of the viral genome. Plants are injected near the meristematic region several times, and the plants are scored for resistance approximately 6 to 8 weeks after inoculation.

A relative rating system scoring method can be used to rate the plants. A zero score means that no symptoms are observed; a one rating means that there is a small blemish that often time is the result of something besides a virus symptom, however, the research cannot be absolutely sure. Plants that fall into categories 0 and 1 are considered resistant. Plants falling into categories 2–4 are considered susceptible. Another method to score plants for resistance is Squash Blot hybridization technique that is well known in the art.

By way of example, and not of limitation, examples of the invention will now be given.

EXAMPLES

Example 1

CONSTRUCTION OF PLANT TRANSFORMATION VECTORS

A portion of the tomato yellow leaf curl virus (TYLCV) was selected and used to create a plant transformation vector. Molecular biology techniques that are well known to those skilled in the art were used to create the plant transformation vector containing a portion of the TYLCV genome. Enzymes used to manipulate DNA can be purchased from either New England Biolabs or Boehringer Mannheim.

Plasmid pTEGC4, containing a portion of the TYLCV genome from an Egyptian TYLCV, was obtained from Dr. Medhat Morkos, from the University of Wisconsin. Plasmid pTEGC4 is a derivative of pBluescriptIIKS, which is a vector that can be purchased from Stratagene. PTEGC4 was created by inserting a fragment of the TYLCV genome into pBluescriptII using a polymerase chain reaction (PCR). During PCR, small differences between the primers and template resulted in the introduction of BamHI restriction sites near the termini of the PCR products. After digestion with BamHI, the PCR fragment was inserted into the BamHI site of pBluescriptII, using routinely-used molecular biology techniques.

The approximately 1.3 kbp BamHI fragment was isolated from pTEGC4 and the fragment was gel-purified. pETO106 is an approximately 12 kilo base pair plasmid, and is a derivative of the commonly used binary vector BIN19 (Bevan, (1984) *Nucleic Acids Res.* 12:8711–8721). Like BIN19, plasmid pETO106 has both a right and left T-DNA border region. These ~25 bp T-DNA regions specify the sites that are recognized by *Agrobacterium tumefaciens*, which mediates the transfer of DNA from the plasmid to the plant chromosome. Infecting a number of different plant tissue types such as leaf discs or cotyledons with *A. tumefaciens* that harbor a binary vector is a preferred method of transforming many plant species. Outside the T-DNA borders, plasmid pETO106 contains the bacterial nptIII gene, which can confer kanamycin resistance to *E. coli* and Agrobacterium that harbor this plasmid.

Plasmid pETO106 was digested with BamHI, and the ~1.3 kbp BamHI fragment from pTEGC4 was cloned into the BamHI site of pETO106 using standard molecular techniques known in the art. One clone obtained from this experiment was designated pETO129.

pETO129 has two cassettes of interest between the T-DNA borders. Starting from the right T-DNA border and proceeding toward the left T-DNA border, the first cassette is a selectable marker cassette composed of three elements that are operationally linked. The first element is the nopaline synthase promoter (P-NOS), which when inserted into the plant chromosome directs the constitutive expression in most plant cells of genes that are positioned downstream of this DNA. The next element is the coding region for the neomycin phosphotransferase type II gene (NPTII). If NPTII is expressed in most plants cells in sufficient quantities, it confers resistance of those cells to the antibiotic kanamycin. The third and final element of the first cassette is the 3' termination end of the nopaline synthase coding region (NOS-T), which contains the polyadenylation recognition site. The selectable marker cassette is commonly used in plant transformation vectors as a selectable marker to identify transformed tissue; the kanamycin resistance conferred to transgenic cells results in a selective growth advantage on medium supplemented with kanamycin.

The second cassette in pETO129 is an effect cassette that two elements. The first element is a portion of the TYLCV genome that composed of 15 bases of untranslated TYLCV DNA located 5' to the C1 initiation codon; the C1 coding region that contains 358 codons, including the stop codon; the C4 coding region, that contains 98 codons, including the stop codon, and parts of the C2 and C3 coding regions. Because of the BamHI cloning, the C2 reading frame was interrupted; however, the reading frame extends beyond the BamHI site. This extension of reading continues as a nonsense reading frame for ~60 bases. Thus, this open reading frame contains 110 codons of the native C2 reading frame, and a nonsense addition of 20 codons, followed by stop codon. Additionally, the C3 reading frame was interrupted by the BamHI cloning, thus, this open reading frame contains 61 codons of the native C3 reading frame, and a nonsense addition into the NOS termination region of an additional 40 codons. The second element of the effect cassette is the 3' termination end of the nopaline synthase coding region (NOS-T).

pETO129 was deposited with the American Type Culture Collection (ATCC), 10801 University Boulevard, Manassas, Va. 2040-2209 on May 2, 1996 and assigned ATCC Deposit Number 97526. This deposit was made in compliance with the Budapest Treaty requirements that the duration of the deposit should be for thirty (30) years from the date of deposit or for five (5) years after the last request for the deposit at the depository or for the enforceable life of a U.S. patent that matures from this application, whichever is longer. pETO129 will be replenished should it become non-viable at the depository.

*E. coli* harboring plasmid pETO129 were mobilized into the disarmed *A. tumefaciens* strain LBA4404 using the triparental mating system to form *A. tumefaciens* pETO129::LBA4404. Transconjugants were used to transform tomato (*Lycopersicon esculentum*).

The effect cassette in pETO129 can be modified to contain a promoter DNA segment, such as the 35S promoter (35S) from cauliflower mosaic virus. Methods for adding such a promoter DNA segment are well known in the art. The use of the 35 S promoter in transgenic virus resistance strategies is both commonly used and well known to those of ordinary skill in the art.

TRANSFORMATION OF TOMATO PLANTS

Tomato seeds were sterilized in 20% Clorox for 20 minutes, rinsed 3 times in sterile distilled water and placed on Murashigi and Skoog medium (Gibco) solidified with 10 grams of Noble agar (Gibco) in 135 mm Phytacon™ tissue culture vessels (Sigma, St. Louis, Mo.). Seeds were germinated for 72 hours at 25° C. in the dark, then moved to a lighted shelf under approximately 80 micromol·m$^{-2}$·s$^{-1}$ PPFD, at 24–26° C. Plant tissue used for transformation was prepared by removing cotyledons from 7-day-old seedlings and cutting them into three parts (proximal, middle and distal to the growing point). The middle and proximal parts were used for co-cultivation with Agrobacterium. They were placed abaxial side down on a sterile filter paper overlaying co-cultivation medium R1F supplemented with 16 g/L glucose, and incubated in the dark for 24 hours. Next, they were incubated for 20 minutes with bacterial inoculum containing 5×10$^8$ CFU/mL of *Agrobacterium tumefaciens*, LBA4404:pETO129, blotted dry, and cultured on the RIF co-cocultivation medium for 48 hours, at 24° C., in the dark.

Bacterial inoculum was prepared by growing *A. tumefaciens*, LBA4404:pETO129, in 25 ml of AB medium (Chilton et al., (1974) *PNAS* 71:3672–3676) supplemented with 50 mg/L kanamycin (K) and 25 mg/L streptomycin (St) (AB$_{K50St25}$) on a shaker at 28° C., 180 rpm, for 24 hours. Bacteria were then pelleted by centrifuging at 8000 rpm for 10 minutes in a Beckman J2-21 centrifuge using a JA-20 rotor. The bacterial pellet fraction was resuspended in a sterile MS medium to a concentration of 5×10$^8$ CFU/mL using a spectrophotometric optical density reading at 550 nm (0.1 OD550=2×10$^8$ CFU/mL). Prior to co-cultivation, the inoculum was supplemented with Acetsyringone (3' 5'dimethoxy-4'hydroxy-acetophenone, Sigma, St. Louis, Mo.) to a final concentration of 600 micromolar.

RESISTANCE SCREENING

Transgenic plants recovered from tissue culture, referred to as the T0 population, were analyzed for the inserted T-DNA. Using the Southern blot technique, which is well known to those skilled in the art, the number of copies that were inserted by the Agrobacterium was determined. Plants with a single-copy insertions of the heterologous DNA segment were kept and selfed. Seed generated from the these T0 selfed plants are called the T1 generation. Between 18 and 27 plants per line were germinated. To test for resistance to TYLCV, T1 seedlings were grown to the two to three leaf stage, and then they were inoculated. Unlike many plant viruses, geminiviruses cannot be transmitted with rubbing with either purified virus, or with sap from infected plants. Instead, plants can be assayed for geminivirus resistance by either growing them in an area with substantial natural pressure, or by placing an insect vector that harbors the virus on or near the plants. The transgenic plants were challenged by yet another method. In this method, young plants are injected with a solution containing Agrobacterium to deliver the viral DNA, which is referred to as Agro-inoculation. The injected Agrobacterium harbor a binary vector that usually contains a full repeat, or at least partial tandem repeat of the viral genome. Plants were injected near the meristematic region several times, and the plants were scored for resistance approximately 6 to 8 weeks post inoculation. Because these are single-copy T1 lines, approximately 25% of the plants are homozygous for the transgenic traits (selectable marker and effect cassettes). Approximately 50% of the plants contain the transgenic traits in a hemizygous state. The remaining 25% of the plants will not contain any transgenic material. Thus, the maximum level of resistance that can be expected using these populations is 75%. It is well known to those skilled in the art that the relative level of resistance observed with many different transgene-mediated viral resistance strategies can be quite variable. Typically, this can range from lines that contain no resistance to lines that cannot be infected. Data from Table 1 show that the population of lines transformed with pETO129 fall within this range of resistance. A relative rating system scoring method was used to rate the plants. A zero score means that no symptoms were observed; a one rating means that there is typically a small blemish that often time is the result of something besides a virus symptom, but the researcher cannot be absolutely sure. The plants that fall into categories 0 and 1 are pooled and called resistant. Plants falling in the progressively more susceptible classes 2–4 are all called susceptible. Lines 1 and 9 are nontransgenic susceptible controls. The number of resistant plants found in lines 1 and 9 are those plants that escaped infection by Agro-inoculation. It is usually assumed that similar numbers of escapes (between 6–16%) would be found in the transgenic lines, which are designed 2–8 and 10–13. Plants that died as a result of other causes were in the "No Result" column as susceptible. Because of this, the estimate of no resistance is a conservative estimate. The results are further illustrated in Table I below.

TABLE I

| Plant Line Number | Total Plants Inoculated | 0–1 Resistant Class | 2–4 Susceptible Class | No Result | % Resistant |
|---|---|---|---|---|---|
| 1 | 18 | 1 | 17 | 0 | 6 |
| 2* | 26 | 7 | 18 | 1 | 27 |
| 3 | 27 | 6 | 18 | 3 | 22 |
| 4 | 26 | 2 | 21 | 2 | 8 |
| 5 | 23 | 6 | 17 | 0 | 26 |
| 6 | 22 | 4 | 18 | 0 | 18 |
| 7 | 24 | 11 | 12 | 0 | 46 |
| 8 | 25 | 15 | 9 | 1 | 60 |
| 9 | 25 | 4 | 21 | 0 | 16 |
| 10 | 22 | 12 | 10 | 0 | 55 |
| 11 | 26 | 15 | 11 | 0 | 58 |
| 12 | 23 | 9 | 10 | 4 | 39 |
| 13 | 26 | 10 | 11 | 5 | 38 |

*Lines 2–8 and 10–13 represent segregating R1 transgenic seed families.

Example 2

This example describes cloning strategies for geminiviruses.

Numerous sequences of TYLCV isolates have been disclosed and would be usefulin creating similar plant transformation vectors to the vector disclosed herein. As disclosed earlier, the Australian isolate of TYLCV was disclosed in Dry et al. (1993) *J. Gen. Virol.* 74:147–151, and the sequence was deposited in Genbank (accession S53251). The sequence of the Indian isolates of TYLCV have been disclosed in Genbank (accessions U15015, U15016 and U15017). The sequence ofthe Israeli isolate of TYLCV has been published in Navot et al. (1991) *Virology* 185:151 –161, and the sequence deposited in Genbank (accession X 15656). The sequence of the Sardinia isolate was published by Kheyr-Pour et al. (1991) *Nucl. Acids. Res.* 19:6763–6769, and the sequence deposited into Genbank (accessions M59838 and M59839). An additional Thailand isolate was disclosed by S. Attathom to Padidam et al. (1995) *J. Gen. Virol.* 76:249–263. The Egyptian and Sicilian isolates were similarly disclosed to Padidam et al. (1995) *J. Gen. Virol.* 76:249–263 by Abdallah and G. Accoto, respectively.

The comparison of geminivirus sequences shown in Padidam et al. (1995) describe the relative similarities between various geminiviruses. These comparisons are useful in designing strategies to clone geminivirus genes for the creation of resistant transgenic plants. Those skilled in the art are familiar using published sequences to design PCR primers to clone unpublished, but similar genes of interest. To clone geminivirus sequences, Rojas et al. have described a method for using degenerate primers in PCR reactions. Rojas et al. (1993) *Plant Disease* 77:340–354.

For example, complete comparison of all sequences would allow for the design of degenerate primers that would facilitate the PCR cloning of all geminivirus sequences that fall into the same class. Alternatively, if one wished to PCR clone the Sicilian isolate, the data in the Padidam manuscript demonstrate that the published Sardinia isolate, which is very similar to the unpublished Sicilian isolate, can be used to design PCR primers that will allow one to clone the Sicilian isolate. Similarly, the published Israeli isolate is shown in the Padidam manuscript to be very similar to the unpublished Egyptian sequence, and can be used to design PCR primers to clone the Egyptian isolate. In this example, the sequence of the Israeli isolate was used to design primers to PCR the Egyptian isolate's C1 gene region. The C1 gene region includes the C1 and C4 open reading frames and portions of the C2 and C3 open reading frames.

Example 3

This example describes how to prepare a plant transformation vector for use in this invention for an uncharacterized tomato-infecting TYLCV isolate.

To clone an uncharacterized tomato-infecting TYLCV isolate, one can isolate DNA from infected tissue. The DNA is then purified. Techniques used to purify geminiviruses DNA from infected plant tissue are well known to those skilled in art. If the virus is isolated in an area close to a region where a viral isolate has been sequenced, one can use the published sequence to design primers to clone the C1 gene region by PCR. In the primer design, small mismatches can be incorporated that will introduce restriction sites near the termini of the PCR-generated population of fragments. The introduction of restriction sites during PCR is a commonly used technique that facilitates the cloning of the fragment into a vector. Those skilled in the art will also realize that the PCR fragment can be easily cloned into a vector without the addition of restriction sites. If one isolated a TYLCV isolate in such areas such as Jordan, Lebanon, Syria or Egypt, one could use the published Israeli sequence (Genbank accession X15656) to design primers to clone the C1 gene region of interest.

An alternative strategy would be to compare all published TYLCV sequences. One would then choose the areas containing the most conserved sequence to design PCR primers. Such an area that is well conserved is the common region. Because the positioning of TYLCV genes is well conserved, similar sequences within the common region and perhaps other regions can be used to synthesize degenerate primers that in a PCR reaction will amplify all, or a specific region of the TYLCV genome. These PCR fragments can be sequenced, and the sequence used to design specific primers to PCR clone the C1 gene region.

Once amplified, the C1 region can be inserted into a plant transformation vector, in the sense orientation upstream of a terminator region that functions in plant cells. Alternatively, the C1 gene region can be inserted in the sense orientation between a promoter region that functions in plant cells and a terminator region that functions in plant cells. A preferred promoter is the 35S promoter, and a preferred terminator is the NOS-T terminator. Those skilled in the art are familar with the various plant transformation vectors and the numerous methods used to deliver the expression cassettes of interest into the plant chromosome. A system commonly used is a binary vector, such as BIN19, with a disarmed *A. tumefaciens* strain, to facilitate the transfer of DNA from the binary vector to the plant's chromosome. It is preferred that the cloning of the PCR fragment, containing the C1 region, into the proper position in the binary vector's expression cassette be performed, and clones selected in *E. coli*. Once the proper plasmid clone has been identified, the binary vector is transformed into a disarmed *A. tumefaciens* strain, as described in Example 1, and the transconjugants used to transform the plant. Tomato plants can be transformed and screened for resistance as described in Example 1.

Example 4

This example describes how to prepare a plant transformation vector containing the C1 gene using a published TYLCV nucleotide sequence.

A synthetic C1 gene region maybe prepared using the published nucleotide sequence of the Israeli isolate as described in Navot, N. et al., (1991) *Virology*, 151–161. Preparation of synthetic sequences using a DNA synthesizer is well known in the art. Once the synthetic sequence is prepared, it is purified, using gel filtration or any other method known in the art.

Once purified, the synthetic C1 gene region can be inserted into a plant transformation vector, in the sense orientation between a promoter region that functions in plant cells and a terminator region that functions in plant cells. A preferred promoter is the 35S promoter, and a preferred terminator is the NOS-T terminator. The sense orientation is defined as the orientation that will allow the promoter to direct the production of messenger RNA that can be translated to give the C1 protein product. Those skilled in the art are familar with the various plant transformation vectors and the numerous methods used to deliver the expression cassettes of interest into the plant chromosome. A system commonly used is a binary vector, such as BIN19, with a disarmed *A. tumefaciens* strain, to facilitate the transfer of DNA from the binary vector to the plant's chromosome. It is preferred that the cloning of the PCR fragment, containing the C1 gene region, into the proper position in the binary vector's expression cassette be performed, and clones selected in *E. coli*. Once the proper plasmid clone has been identified, the binary vector is transformed into a disarmed *A. tumefaciens* strain, as described in Example 1, and the transconjugants used to transform the plant. Tomato plants can be transformed and screened for resistance as described in Example 1.

The foregoing is intended as illustrative of the present invention but not limiting. Numerous variations and modifications can be effected without departing from the true spirit and scope of the novel concepts of the invention.

I claim:

1. A plasmid designated pETO129 having ATCC Accession Number 97526.

\* \* \* \* \*